(12) United States Patent
Amo et al.

(10) Patent No.: US 9,297,785 B2
(45) Date of Patent: Mar. 29, 2016

(54) METHOD FOR DETECTING ATMOSPHERIC VAPORS AT PARTS PER QUADRILLION (PPQ) CONCENTRATIONS

(75) Inventors: Mario Amo, Boecillo (ES); Daoiz Zamora, Boecillo (ES); Alejandro Casado, Boecillo (ES); Gonzalo Fernandez de la Mora, Madrid (ES); Guillermo Vidal-de-Miguel, Madrid (ES); Juan Fernandez de la Mora, New Haven, CT (US)

(73) Assignee: Sociedad Europea de Analisis Diferencial de Movilidad, Madrid (ES)

( * ) Notice: Subject to any disclaimer, the term of this patent is extended or adjusted under 35 U.S.C. 154(b) by 587 days.

(21) Appl. No.: 13/532,146

(22) Filed: Jun. 25, 2012

(65) Prior Publication Data

US 2012/0325024 A1    Dec. 27, 2012

Related U.S. Application Data

(60) Provisional application No. 61/500,931, filed on Jun. 24, 2011.

(51) Int. Cl.
| | |
|---|---|
| *G01N 1/20* | (2006.01) |
| *G01N 27/62* | (2006.01) |
| *H01J 49/16* | (2006.01) |
| *G01N 33/00* | (2006.01) |

(52) U.S. Cl.
CPC .......... *G01N 27/622* (2013.01); *H01J 49/165* (2013.01); *G01N 33/0057* (2013.01)

(58) Field of Classification Search
CPC ... B01D 29/01; G01N 1/4077; G01N 1/2035; G01N 1/2258

USPC .................................................. 73/863.24
See application file for complete search history.

(56) References Cited

U.S. PATENT DOCUMENTS

| | | | |
|---|---|---|---|
| 5,345,809 A * | 9/1994 | Corrigan et al. ........... | 73/23.2 |
| 2006/0192097 A1 | 8/2006 | Anttalainen | |

(Continued)

OTHER PUBLICATIONS

Pal Tamas Szabo et al: "Electrospray mass spectrometry of hydrophobic compounds using dimethyl sulfoxide and dimethylformamide as solvents" Rapid Communications in Mass Spectrometry, vol. 15, Nov. 20, 2001, pp. 2415-2419, XP55042578 DOI: 10.1002/rcm.526.

*Primary Examiner* — Hezron E Williams
*Assistant Examiner* — Rodney T Frank
(74) *Attorney, Agent, or Firm* — Hoffmann & Baron, LLP

(57) ABSTRACT

Improvements are provided in the detection of atmospheric vapors by ionizing them near ambient pressure, and analyzing them as ions. Lowest detection limits of parts per quadrillion (ppq) concentrations are enabled by a combination of improvements, including the use of a filter to remove occasional intense signal from explosive particles. Several sources of chemical background are identified and solutions for their reduction or elimination are presented. Gains in response time may be achieved by operating at elevated temperature. When the ionizer is an electrospray source, the use of high boiling point solvents is indicated. An increased selectivity is achieved by operating a differential mobility analyzer (DMA) in series with a mass spectrometer. However, ppq sensitivities require various improvements in the DMA system including a special coupling to the ionizer, controlling the temperature in the DMA pump circuit, avoidance of induction on the DMA electrodes from heating devices, etc.

11 Claims, 7 Drawing Sheets

(56) References Cited

U.S. PATENT DOCUMENTS

| | | |
|---|---|---|
| 2007/0029477 A1 | 2/2007 | Miller et al. |
| 2008/0101995 A1 | 5/2008 | Gabowitcz et al. |
| 2009/0248319 A1* | 10/2009 | Call et al. .................. 702/22 |
| 2010/0176290 A1 | 7/2010 | Vidal-De-Miguel |
| 2011/0186436 A1* | 8/2011 | Novosselov et al. ......... 204/600 |

* cited by examiner

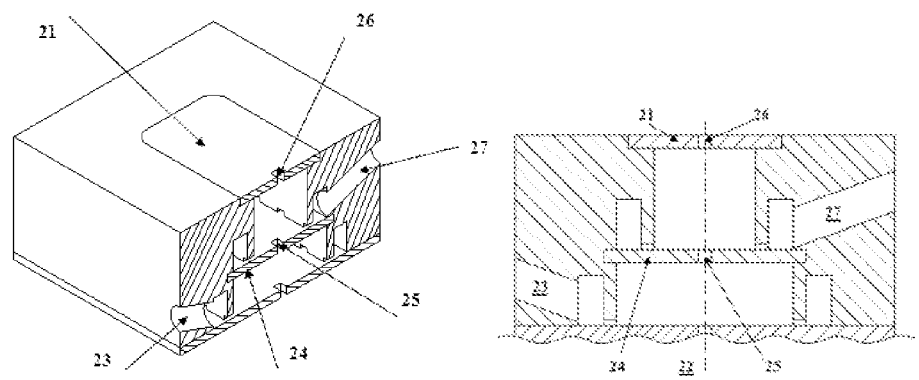
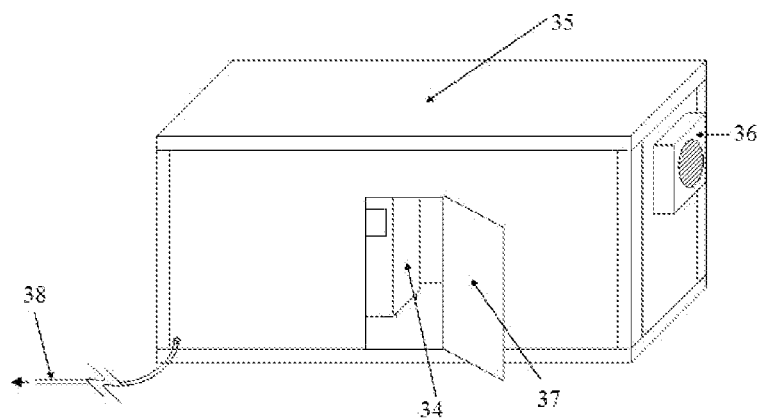
FIG 8
FIG 9

METHOD FOR DETECTING ATMOSPHERIC VAPORS AT PARTS PER QUADRILLION (PPQ) CONCENTRATIONS

CROSS-REFERENCE TO RELATED APPLICATION

This application claims priority to U.S. Provisional Patent Application No. 61/500,931, filed Jun. 24, 2011, the entire contents of which is incorporated herein by reference.

US PATENTS AND PATENT APPLICATIONS CITED

U.S. Pat. No. 7,855,360, J. Fernández de la Mora, A. Casado, G. Fernández de la Mora, Method to accurately discriminate gas phase ions with several filtering devices in tandem, issued Dec. 21, 2010.

US Patent Application 20100264304, P. Martinez-Lozano and J. Fernandez de la Mora, Method for detecting volatile species of high molecular weight.

U.S. patent application Ser. No. 12/686,669, G. Vidal-de-Miguel 2010, Ionizer for vapor analysis decoupling the ionization region from the analyzer. Publication No: US-2010-0176290-A1 Jul. 15, 2010.

U.S. patent application Ser. No. 11/786,688, J. Rus, J. Fernandez de la Mora, Resolution improvement in the coupling of planar differential mobility analyzers with mass spectrometers or other analyzers and detectors. 11 Apr. 7. Publication 20080251714, October 2008. Allowed, January 2011.

U.S. Pat. No. 7,928,373, J. Rus, J. Fernandez de la Mora, Resolution improvement in the coupling of planar differential mobility analyzers with mass spectrometers or other analyzers and detectors. Issued Apr. 19, 2011.

OTHER PUBLICATIONS CITED

E. Mesonero, J. A. Sillero, M. Hernandez, J. Fernandez de la Mora, Secondary electrospray ionization (SESI) detection of explosive vapors below 0.02 ppt on a Triple quadrupole with an atmospheric pressure source, in: Poster Presented at the ASMS Annual Conference, May 31-Jun. 4, 2009, Philadelphia, Pa., 2009.

Wittmer, D.; Chen, Y.-H.; Luckenbill, B. K.; Hill, H. H., Jr. *Anal. Chem.* 1994, 66, 2348.

C. Wu, W. F. Siems, H. H. Hill Jr., Secondary electrospray ionization ion mobility spectrometry/mass spectrometry of illicit drugs, Anal. Chem. 72 (2000) 396-403.

Juan Fernandez de la Mora, Ionization of vapor molecules by an electrospray cloud, Int. J. Mass Spectrom., 300 182-193 (2011).

J. A. Riddick, W. B. Bunger, T Sakano 1986, Organic solvents: Physical Properties and Method of Purification, $3^{rd}$ edn. Wiley-Interscience.

J. Fernández de la Mora, and I. G. Loscertales, The current emitted by highly conducting Taylor cones, J. Fluid Mechanics, 260, 155-184, 1994.

J. B. Fenn, M. Mann, C. K. Meng, S. K. Wong, C. Whitehouse (1989) Electrospray ionization for mass spectrometry of large biomolecules, *Science* 246, 64-71.

B. K. Ku, J. Fernandez de la Mora, D. A. Saucy and J. N. Alexander, IV, Mass distribution measurement of water-insoluble polymers by charge-reduced electrospray mobility analysis, Analytical Chemistry, 76, 814-822, 2004.

S. Ude, J. Fernandez de la Mora, J, N. Alexander IV, D, A. Saucy, Aerosol size standards in the nanometer size range: II, Narrow size distributions of polystyrene 3-11 nm in diameter, J. Colloid and Interface Sci., 293, 384-393 (2006).

J. Fernandez de la Mora, Fluid dynamics of electrosprays, Annual Review of Fluid Mechanics, 39, 217-243 (2007).

J. B. Fenn, M. Mann, C. C. Meng, C. F. Wong and C. M. Whitehouse, electrospray ionization for mass spectrometry of large biomolecules, Science, 246 (4926), 64-71, 1989.

P. Martinez-Lozano, J. Rus, G. Fernández de la Mora, M. Hernández, J. Fernández de la Mora, Secondary Electrospray Ionization (SESI) of Ambient Vapors for Explosive Detection at Concentrations Below Parts Per Trillion. J. Am. Soc. Mass Spectr. 2009, 20, 287-294

FIELD OF THE INVENTION

This invention relates to the detection of chemical species present in vapor form in the atmosphere.

BACKGROUND OF THE INVENTION

The detection of vapor species present in the atmosphere is of great interest in numerous applications. It is the basis of olfaction in the biological world. Man's sense of smell is relatively weak, so the most demanding aspects of this function must be taken up by various artificial detectors. Examples of the actual or potential usefulness of vapor detectors are clear in various fields, such as food and aromas; medical diagnosis; security applications (explosive detection, person recognition, identification of pathogens, etc.); monitoring of atmospheric pollutants, etc.

The detection of vapors becomes increasingly difficult when they are present at decreasing concentrations in a gas (i.e. the atmosphere) for two reasons. First, one needs an increasingly more sensitive detector. Second, the number of competing vapors present in the atmosphere (or other complex gaseous mixtures) at concentrations comparable to those of the target vapor increases rapidly as the concentration of the target vapor decreases. Consequently, the discriminating power or resolution of the detector must increase along with its sensitivity. Few detectors have been available capable of sensing vapors at concentrations below parts per billion (1 ppb=$10^{-9}$ atmospheres of partial pressure). This is a concentration range at which animals such as dogs are believed to often be still sensitive, and at which many useful vapor detection tasks can be performed. Many other applications require detecting still smaller concentrations down to parts per trillion (1 ppt=$10^{-12}$ atmospheres of partial pressure) or parts per quadrillion (1 ppq=$10^{-15}$ atmospheres of partial pressure). This is necessary, for instance, to detect low vapor pressure substances such as plastic explosives. The most advanced state-of-the-art artificial detectors of substances in the atmosphere are used for security screening of explosives in the civil aviation field, and are called Explosive Trace Detectors, or ETDs. ETDs are based on ion mobility spectrometers (IMS), and though they claim sometimes the ability to detect low volatility materials, generally do not do so directly in the gas phase through olfaction. Rather, detection is achieved by swiping a target surface with a cloth in the hope of collecting some condensed sample of the target substance (typically one or several microscopic particles). The cloth is then introduced into a heated region where any particle present is volatilized, ionized and detected.

The most advanced state-of-the-art detectors for low volatility substances are the explosive detectors used for airport explosive screening, since they target, among others, plastic explosives, whose vapor pressure is extremely low. All airport ETD detectors currently deployed rely on high speed gas jets or on swabbing for sampling from surfaces, with the obvious goal of dislodging small particles from the person or object probed. A device relying on vapor analysis would simply sample the gas from the vicinity of the suspected point, without the help of auxiliary jets which necessarily greatly dilute the sample vapor.

The particle collection occurrence is highly randomized in real environment. The amount of target substances (or contaminants) that present detectors measure depends on the size and number of particles collected, which is highly variable between tests. As a result, the signals produced by particle based detectors are highly scattered, and the operator needs to increase the detection thresholds accordingly. As a result, the Probability of Detection (PoD) and the False Alarm Ratio (FAR) of these detectors become very poor.

As reported in June 2010 by Mr. Steve Lord, Director Homeland Security and Justice Issues, before the House of Representatives [Subcommittee on Transportation Security and Infrastructure Protection, Committee on Homeland Security, GAO-10-880T; see web page http://www.gao.gov/new.items/d10880t.pdf)], there is currently no technology approved or qualified by TSA to screen cargo once it is loaded onto a ULD pallet or container. Pallets and containers are common means of transporting air cargo on wide-body passenger aircraft. Prior to May 1, 2010, canine screening was the only screening method, other than physical search, approved by TSA to screen such cargo. However, TSA officials still have some concerns about the effectiveness of the canine teams, and effective May 1, 2010, the agency no longer allows canine teams to be used for primary screening of ULD pallets and containers. The Transport Security Administration (TSA), (see web page http://www.tsa.gov/assets/pdf/non_ssi_acstl.pdf) has produced a document entitled "TSA Air Cargo Screening Technology List (ACSTL)", which defines the technologies accepted for air cargo screening. In the first page of this document, the TSA declares the following: "Despite what some manufacturers advertise, TSA has not approved any equipment for any ULD screening. The maximum size cargo configuration that may be screened is a 48"×48"×65" skid." A ULD is a well known acronym in the air cargo community; it stands for "Unit Load Device", and is a pallet or container used to load luggage, freight, and mail on wide-body aircraft. It can be understood as a precise definition of specific containers used for aircrafts. One can therefore conclude that no detection method presently exists for explosive screening of containers for air cargo, neither canine, nor technology-based.

We have for some time expressed our view that vapors can be detected at ppt concentrations, but have met wide skepticism from the experts. No instrument comparable in sensitivity with the one described in this invention has been available to others to discover what it takes to go from the barely credible ppb detection level down to the ppt level, not to speak of the ppq sensitivities aimed at in this invention.

In contrast, the focus of the present invention is on the detection of species present in the gas phase as vapors, rather than of species present on a surface in solid or liquid form. Vapors diffuse smoothly and produce much more repeatable signals that allow the operator to reduce detection thresholds. This pure gas phase approach had for a long time been considered as hopeless for detection of low volatility substances. However, we have recently demonstrated its suitability in certain situations to detect volatiles at concentrations below 1 ppt (Mesonero et al. 2009). Initially we used a sensitive mass spectrometer having an atmospheric pressure source (API-MS) preceded by an ionizer. In a preferred embodiment, vapor ionization was achieved by putting the gas to be analyzed in contact with a cloud of charged particles produced by electrospray (ES) ionization (Fenn et al. 1989). Although a sensitivity to sub ppt concentrations was unprecedented, we found that detection at these concentrations still made use of a very large number of individual molecules, on the order of $10^8$. A lowest detection level in the ppt range therefore implies a sensing efficiency of $10^{-8}$. The room and the need for substantial improvements are therefore clear. We reported two kinds of barriers to achieving improved sensing efficiencies. One was a low vapor ionization probability of the order of $10^{-4}$ (i.e., only one in $10^4$ vapor molecules contained in the sample volume passed through the ionizer and become an ion sucked into the mass spectrometer). This difficulty has been alleviated by an improved Secondary Electrospray Ionization (SESI) scheme, taught in U.S. patent application Ser. No. 12/686,669 by Vidal. The other obstacle was the impossibility to distinguish the signal of a target molecule from that of other species having a similar chemical signature (chemical noise). The use of Differential Mobility Analyzer (DMA) in tandem with MS-MS also alleviated this problem. As described in U.S. Pat. No. 7,855,360, the use of these three narrow band ion filters in series (DMA-MS-MS) produces a drastic reduction in chemical noise, without significant penalty (with respect to an analysis based on a single or a triple quadrupole MS alone) in terms of analysis time and ion transmission.

The first experimental system incorporating a Sampler preconcentrator, a desorber, and a SESI-DMA-MS-MS ionizer and analyzer used for our preliminary explorations, and which is incorporated in the present invention, was unique in the world in its ability to sense vapors at concentrations below 1 ppt. However, systematic work with this apparatus and its subsequent improvements have provided for the first time a clear picture of a number of previously unsuspected difficulties:

i) Sampler contamination. Consider for concreteness an attempt to detect the presence of the plastic explosive RDX as a vapor in the atmosphere. Its equilibrium vapor pressure at ambient temperature is quoted to be in the range of a few ppt (This value, however, must be taken as provisional, as no reliable method to measure such a low vapor pressure has been available prior to the development of our detector). There are many thousands of other vapors present in the ambient at higher partial pressures that could produce background signals. However, we were able to determine confidently after DMA-MS-MS analysis that at least part of the background signal remaining in the detector after removal of the source of RDX vapor was due to contamination of the analyzer with RDX itself. This forced us to review with exquisite care all possible sources of RDX contamination resulting from previous tests with RDX samples. We had of course followed conventional practices to avoid contamination from samples. In particular, all gas lines were heated to remove any RDX deposited and absorbed on the walls of the system during a measurement with RDX vapor. However, at the unusual sensitivity levels of our instrument, these common practices were clearly insufficient. Eventually we discovered several sources of contamination in the sampling system. Most important was the fact that, upon removing the filter from the sampler, some RDX collected on the filter was transmitted to the surface of the filter holder and remained there as a contaminant. Then, on introducing a new clean filter to collect a new sample of ambient air, part of the RDX contaminant left on the sampler was transferred to the new filter. Sometimes vapors or particles of RDX were collected on the walls of the sampler. In this case there was no direct or indirect contamination of the filter via condensed phase contact. But the finite vapor pressure of the adsorbed RDX molecules and particles led still to a sufficient release of RDX vapors from the contaminated sampler surfaces into the sampled gas and from this gas into the collecting filter. These forms of contamination were always indirect, and therefore weak and hard to detect. But they were certainly sufficient to preclude detection levels in the ppq range, and could be unambiguously identified with our sensitive instrument, particularly after careful cleaning and decontamination. Another subtler form of indirect contamination was subsequently discovered. Upon completing a sampling experiment on a particular filter, the pump sampling the air at the exit of the sampling system was stopped. Occasionally, however, ambient gas entered backwards into the system, moving upstream from the pump into the sampler. This backward flow resulted in contamination of the sampler very much as when RDX contamination came from upstream.

ii) Ambient contamination. Many other conventional practices need to be refined for vapor detection at ppq levels. Military installation rooms presumed to be clean, where explosives had been manipulated in the past, were found to be heavily polluted. We therefore have often installed the analyzer in its own external cabin, whose cleanness we could more easily control. Even so, we found that this cabin tended to become contaminated after several days of analysis of samples. As a consequence, background levels measured rise and so does the detection threshold. Similar problems may be encountered in various operational scenarios. For instance, when sampling large volumes from a truck or other large containers, the effluents from the sampling pump, if improperly handled, may artificially contaminate a neighboring truck or cargo container.

An important aspect in the development of ppq level detectors is their test with standards. This invention is therefore concerned not only with the improvement of unusually sensitive vapor detectors, but also with the development of methods to rigorously test such detectors. Careful avoidance of contamination is as relevant in such testing grounds as in the analyzer cabin just discussed. Contamination can arise from the most unsuspected sources. For instance, we find that dogs trained to detect RDX and believed to be capable of actually detecting it, are in fact detecting trace quantities of other far more volatile explosives such as TNT or EGDN, accidentally present in the training sample of RDX. Careful examination of the sample handling procedure confirms the likelihood of slight cross contamination between the low volatility and the high volatility test samples. The sample may be polluted even without physical contact, for instance when a volatile and an involatile sample are placed in a common container, since the volatile sample can diffuse through the gas and adsorb on the surfaces of the container or the other solid samples held within it. One can hence easily envision situations where certain seemingly effective detectors could in fact have been for long periods entirely ineffective with uncontaminated low volatility samples. Standards for such tests need therefore to be handled with unusual care. For biological or other non-chemically specific (i.e. non-MS) detectors, testing samples must be analyzed periodically with chemically specific detectors in order to confirm the lack of such cross contamination. Many other subtle contamination schemes have been found during our studies. For instance, testing for explosives is frequently carried out in specialized facilities, often in closed buildings with unusually large volumes and little ventilation. Boxes of various shapes and volumes containing substantial quantities of explosive sample are then introduced into such buildings, and the interior volumes of such boxes are sampled in various forms. If the gas leaving the pump of the sampler pre-concentrator exits directly into the testing building, it contributes to its background, since the collector collects typically less than half of the vapor sample.

iii) Particulate associated chemical noise. Most samplers used for trace detection are primarily based on collecting and detecting particles. The reason is that their modest sensitivity precludes direct vapor detection, whence, their only hope to detect low vapor pressure substances is to collect them in the form of particles, typically carrying far more mass than the vapor molecules in the gas. Conventional samplers often use a pre-filter. Since particles are the main source of detected low vapor substances, the aim of this filter is evidently not to remove small particles potentially carrying the target substance. Its purpose is rather to remove relatively large organic objects, such as insects or their fragments, whose capture in the filter would overwhelm and often seriously contaminate the analytical system. The size of the particles typically intercepted by the pre-filter in such samplers varies from one to the other. Generally, explosive-bearing particles are believed to have sizes from a few microns to hundreds of microns. Explosive vapors are generally sticky, so they tend to attach to particulate matter, and by aerodynamically removing such particles from a surface one hopes to collect a measurable amount of explosive. It is therefore desirable to collect as much as possible of the suspended particles to maximize the amount of explosive collected on their surface. This desire must of course be moderated somehow to minimize the risk of capturing large chunks of organic matter, which upon heating would release inordinate doses of volatile contaminating materials. A reasonable cutoff size for the pre-filter is therefore certainly to remove debris in the mm size range. More conservatively, samplers tend to remove even smaller particles, typically down to 100 µm. One rational for this lower size range is that larger particles settle rapidly into the floor, are harder to bring into the gas phase, and after being aerosolized tend to settle along the sampling lines or impact on their curved sections. The potential advantage of sampling particles larger than 100 µm therefore rarely compensates for the associated contamination risks. Consequently, a typical pre-filter will retain particles larger than 100 µm, and pass most of the smaller particles for their potential content of the target substances to be captured on the main filter. In other words, sampling systems for low vapor pressure substances typically rely on particle collection in the size range below 50-100 µm. In many detection applications, one must set a threshold concentration to launch an alarm. In order to avoid false alarms, this threshold must be higher than the background. But if the background rises (even rarely) every time a big particle of chemical interfering species is captured, the threshold needs to be raised above this value. And under such circumstances the lower detection level of the system is not set by the real sensitivity of the detector, but by the high threshold required to reduce the FAR.

iv) Electrospray limited temperature. Following detection of a low vapor pressure substance, the detector often tends to give a positive leftover signal for that substance. This leftover or memory effect decreases steadily over time, but does not fall to zero for extended periods due to adsorption into and slow release of the vapor from the walls of the analyzer. In order to accelerate the complete decay to zero of this leftover signal, IMS systems and other analytical devices often operate at elevated temperatures, at which adsorbed vapors are rapidly released into the gas. It is accordingly important to heat all system components where such adsorption could take place.

One of the most effective vapor ionization sources available, often referred to as a Secondary Electro-Spray Ionizer (SESI), simply mixes the sample vapors with a cloud of charged droplets of a relatively clean volatile solvent (Fernandez de la Mora 2011). Other more common ionizers rely on an electrical discharge or a radioactive source, often based on a foil of $^{63}$Ni. These two later ionizers are readily heated, but not the first. Indeed, an electrospray source requires that the electrosprayed solvent be in liquid form, which forces an operational temperature below its boiling point. It is important that all parts of the ionizer in contact with the sample gas be hot, ideally at a temperature in the range of 150° C., preferably higher. This is well above the boiling point of most common solvents, certainly those previously used for SESI applications. Wittmer et al. (1994) have developed a water cooled electrospray source, which has been used by Wu et al. (2000) for vapor ionization. Still, the sample gas cannot flow over the water-cooled regions (including the tip of the Taylor cone where the ionizing spray drops are produced), as cold surfaces would trap the gas and lead to the undesirable memory effect one seeks to avoid via heating. Mixing between the sample gas and these charged drops (or the ions they release after drop evaporation), must therefore occur downstream from the ion source, in an uncooled region. However, as shown by Fernandez de la Mora (2011), ionization is considerably more effective when the vapor to be ionized is present at the very tip of the Taylor cone. Achieving this more efficient condition hence requires an approach free from cooled surfaces.

v) Contamination from the electrospray solvent and nitrate-based explosives. SESI-based ionization of vapors offers certain advantages over corona ionization. First, because of the absence in SESI of energetic and potentially reactive phenomena taking place in the corona region, where impurity species may be created from preexisting vapor species in the sample. Another advantage of SESI is that certain additives introduced in the electrosprayed liquid readily produce desired reagent ions in the gas phase. For instance, a good option for ionizing many explosives is to produce halogen ions (i.e. $Cl^-$) by seeding them into the electrospray solvent in salt or acid form (i.e., NaCl or HCl). The acid form is generally preferable because acids are far more volatile than salts so the spray of drops produces fewer solid residues. However, we find that commercial aqueous HCl is typically supplied with considerable proportions of impurities of sulfates, nitrates and other inorganic anions. This is true even for specialty reagents used for metal analysis, which have indeed very small levels of metal cation contaminants, but still contain substantial quantities of anions such as nitrate. The $NO_3^-$ ion is therefore abundantly formed upon electrospraying such solutions. This impurity ion interferes with the detection of nitrate explosives, typically represented in the gas phase by its volatile decomposition products $NO_3H$ and $NH_3$. Indeed, $NO_3H$ vapor ionizes into $NO_3^-$ in negative ionization, so solution and gas phase nitrate are indistinguishable, posing a difficult obstacle to the successful sniffing of ammonium nitrate. A first step to the solution of this serious interference is to identify nitrate-free halides, which can indeed be obtained. This is however insufficient to safely sniff ammonium nitrate explosives because other abundant sources of nitric acid exist in the atmosphere. It is in fact well known that ammonium nitrate itself forms naturally in the atmosphere over polluted sites where ammonia and nitric acid preexist at sufficient concentration.

The problem of detecting vapors in the ppq level is currently not solved. It is commonly believed by those skilled in the art that detection of vapors at the ppq level in real environments is impossible. Moreover, substances with low vapor pressures such as plastic explosives are believed to be non-volatile, and their detection is based on particle collection and detection, however, particle detection occurrence is highly randomized, and particle based explosives detection is not functional in the real field.

Consequently, one purpose of this invention is to teach how to detect atmospheric vapors by means of a system built from a Sampling system which acts as pre-concentrator, a primary filter which retains vapors and vehicles information from the sampling system to the Analyzer, and an Analyzer incorporating a thermal desorber, a SESI ionizer, and a DMA-MS-MS analyzer. Other purposes of the present invention are to teach:

(i) how to prevent sampler contamination,
(ii) how to prevent contamination of the analyzer through the atmospheric background during operation,
(iii) how to prevent chemical noise produced by aerosol particles present in the air to be analyzed,
(iv) how to prevent contamination produced by the electrospray used in some embodiments of the invention, and
(v) how to operate a SESI at high temperature, so as to detect low volatility species directly in the gas phase and at concentrations down to the ppq level.

SUMMARY OF THE INVENTION

A first aspect of the invention constitutes a detector for vapors, sensitive below parts per trillion (ppt) concentrations, and which can reach sensitivities below parts per quadrillion (ppq) for certain volatiles. The aim of this detector is to determine the concentration of volatiles of interest within a gas, which typically is air. This detector is built from three basic units illustrated in FIG. 1: (i) A sampling system, (ii) A primary filter, and (iii) An Analyzer. The sampling system and the Analyzer are physically independent units, while the primary filter vehicles the information from the sampling system to the Analyzer. The sampling system extracts gas from the target to be analyzed, which can be the atmosphere, or any partially confined or closed environment such as a house, a truck, a container, etc., and deposits vapors within this gas in the primary filter. At the end of the sampling process, the primary filter is extracted from the sampling system, and inserted into the Analyzer, which can be physically separated from the sampling system. Once the primary filter is inserted into the Analyzer, this unit determines the concentration of the volatiles of interest up to concentrations of 1 ppq.

The sampling system extracts selected vapors from the sampled gas, preferably after passing this sampled gas through a prefiltering stage, which may be in the form of a prefilter, aimed at removing particles larger than a certain threshold size. The sample gas then goes through a primary filter intended to trap vapors. The prefilter could alternatively be substituted by an impactor in the prefiltering stage. A preferred size cutoff for the prefiltering stage is 25 μm, preferably 10 μm. One preferred embodiment of the sampling system uses a disposable holder for all components upstream of the primary filter and a diversity of approaches to reduce various subtle sources of contamination. The second unit of the detector is the primary filter, which traps the molecules of low volatility vapors because they are naturally bound to it. The filter can be made of TENAX, stainless steel, fiber glass, or other materials selected by those skilled in the art to trap the desired vapors.

The third unit is the Analyzer, which is self-contained, and incorporates the following components: (i) A thermal desorber, (ii) A high temperature ionizer, and (iii) An atmospheric pressure ionization mass spectrometer, preferably preceded by a mobility filter. The function of the thermal desorber is to liberate the vapors collected on the primary filter into a stream of clean gas, and to transport these vapors to the high temperature ionizer. The high temperature ionizer is an ionization source, whose function is to turn some of the vapor molecules into ions. A preferred ionizer relies on a cloud of charged drops formed from electrospraying a solvent with boiling point of 150° C. or more, but other options are also included. A third component of the Analyzer is an atmospheric pressure ionization mass spectrometer, preferably preceded by a mobility filter.

A second aspect of the invention makes use of the know-how associated to the sensitive detector just described to develop a method to evaluate other detector systems with lower detection levels below 1 part per trillion, even to detect levels in parts per quadrillion.

BRIEF DESCRIPTION OF THE DRAWINGS

FIG. 1 also shows the transport of the primary filter from the sampling system to the Analyzer.

FIG. 8 Shows details on how to maintain the symmetry of the impinging flows below plate (21) when the analyzer is a DMA with a rectangular slit.

FIG. 9 shows the environment surrounding the components of the detector of FIG. 3, designed to minimize contamination of its components.

DETAILED DESCRIPTION OF THE INVENTION

Figure 3:
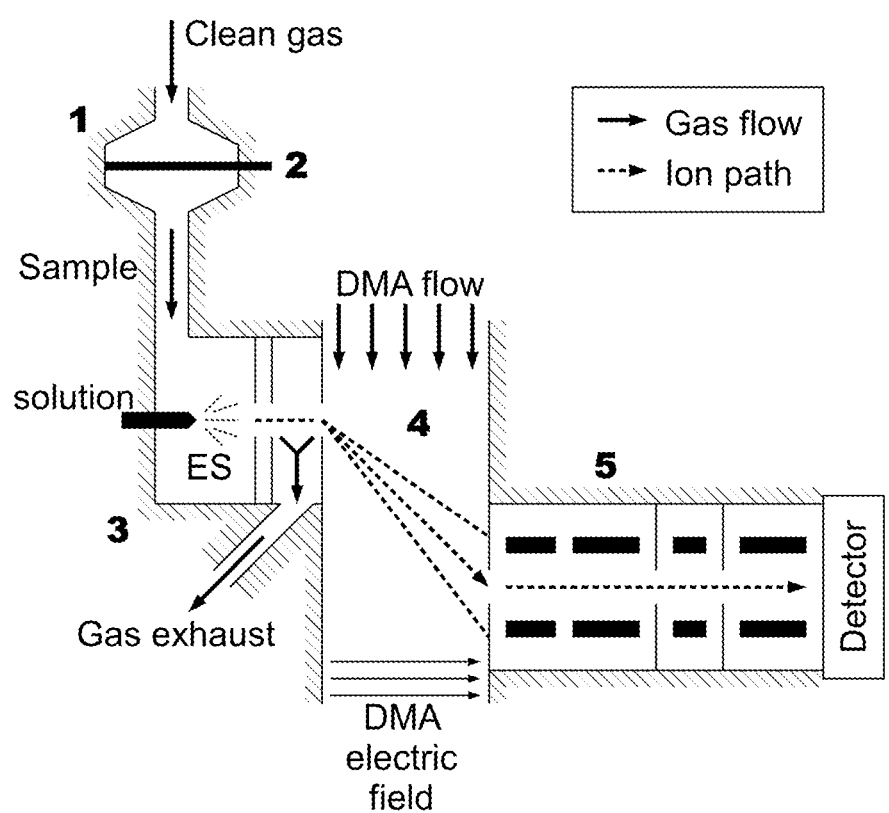
FIG. 3 is a schematic of the components of the Analyzer, showing a desorption system where the vapors collected in a filter by the sampling system are heated, released and conveyed by a small flow of gas into the ionizer, and then to the DMA-MS-MS system.

A sketch of the Analyzer used for vapor detection is given in FIG. 3, showing a desorption system (1) where the vapors collected in a filter (2) by the sampling system are heated, released and conveyed by a small flow of gas into the ionizer (3), the DMA (4) and the MS system (5), where several target species are detected sequentially during the desorption period. The effectiveness of the analyzer used in the present invention is increased by incorporating a sampling system departing in several ways from conventional samplers.

Low cut-off pre-filter: One solution adopted to remove the large statistical noise produced by aerosol particles according to the present invention is to remove essentially all the particles with a pre-filter having the lowest practical size cut. This is equivalent to base the detection mostly on vapor molecules rather than on both particles and molecules. A less extreme alternative is to remove only the largest particles, whose low frequency of appearance causes the largest statistical noise. In general, however, we find that for systems like ours, sensitive well below 1 ppt of vapor pressure, the lower the cut of the pre-filter the better the results. There are of course practical considerations familiar to those skilled in the art of filtration. Filtering particles in the range from 0.1 μm up to 1-5 μm is relatively difficult, often harder than removing vapors. The reason is that the diffusivity of vapors is much larger than that of particles. Accordingly, particles small enough not to be trappable by phenomena other than diffusion (inertia, interception, etc.) require filters in which vapors are more efficiently caught than the particles themselves. These considerations therefore call for the adoption of practical limits to the smallest particle size to be removed by the pre-filter. A variety of solutions to remove the particles and pass efficiently the vapors are available to those familiar with the art. One is to use filter materials which are inert towards the vapor. In this case, vapor molecules do occasionally collide with the filter, but they re-evaporate and are not captured. This approach is effective with reasonably inert vapors, but is harder with other reactive or sticky vapors. An alternative approach is to use a pre-filter with a cutoff size from a few tens of μm down to one or a few μm, preferably 10 μm. This size range leads to acceptable pressure drops and tolerable vapor losses in the pre-filter. With such pre-filters we have greatly decreased the lowest detection levels for vapors compatible with a minimal level of false alarms. A pre-filter with an uncommonly small cutoff size is therefore an important component of the present invention. An aerosol impactor with a comparable size cut would also serve as a prefilter, with the advantage that its impact surface could be relatively small, and vapor losses by diffusion would be substantially lower than in a filter. Another advantage of impactors is that the particle size cut-off can be easily defined and be well below 1 micron, with a manageable corresponding pressure drop. Both in the case of impactors and prefilters, the material collected in the filter or the impaction plate could, if desired, also be used for separate analysis.

We note an important additional advantage of detection systems primarily based on vapor sensing, over systems relying on the capture of particles. In a situation of positive detection of a large improvised explosive device, the particle sampling components of the detector in contact with a person or luggage cannot be hot. Yet, some of these components may collect large doses of particles, becoming highly contaminated and inoperable for an extended cleanup period. This situation is almost inevitable in a passenger portal where a substantial quantity of explosive is introduced by the passenger. The usual particle removal system involves various high speed jets that will dislodge the particles from the subject. Some of these particles will be ingested into the heated components of the analyzer, but many others will inevitably acquire relatively high speeds from the jet, and be thrown into the walls of the portal. There they will remain as long term contaminants until a special cleanup is implemented. In contrast, all critical non-disposable components of our particle-free system are fully heated, and recover very fast (~1 min) from high concentration events without the need for an ad hoc cleanup.

Contamination upstream the primary filter was reduced or eliminated by various schemes. One method that offered improvements was heating the sampler to elevated temperature while passing gas through it in order to remove all contamination from prior measurements. This approach was most effective with moderately volatile explosives such as EGDN and TNT. In general, and particularly for the least volatile explosives such as RDX and PETN, the best solution found to eliminate upstream contamination was the use of a new disposable filter holder for every new sample taken. Downstream contamination by the same procedure would require a disposable pump. A more practical solution is the installation of a unidirectional valve (8), or any alternative system precluding backflow from the pump into the sampler. Once these precautions were implemented according to this invention, we were able to maintain a relatively consistent level of background signal before and after sampling vapors of RDX (or other substance of interest) into the detector.

Figure 1:
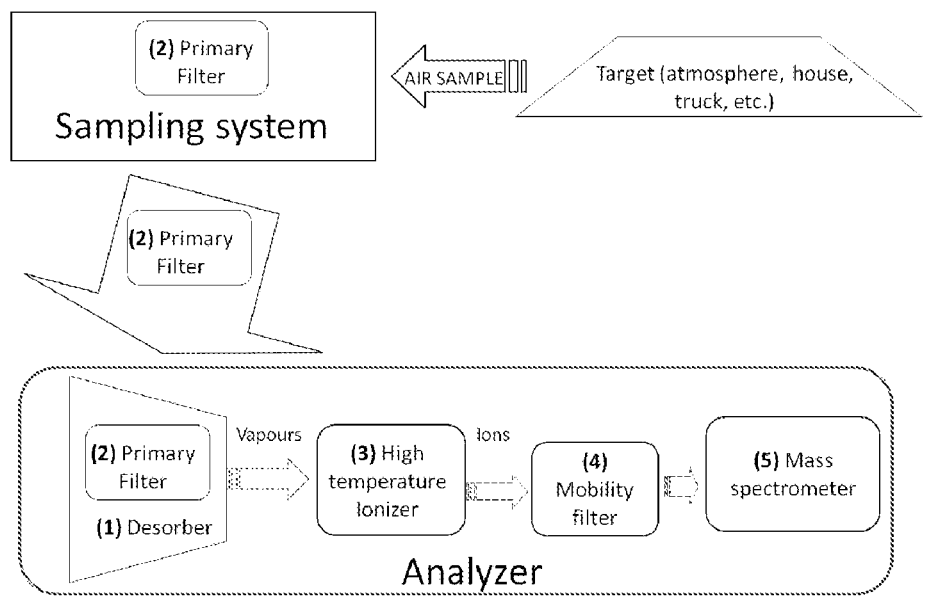
FIG. 1 is a schematic of the complete detector, showing the sampling system, the primary filter and the Analyzer, along with the main elements within the Analyzer: Desorber, Ionizer, and the Mass Spectrometer with a mobility filter.
Figure 2:
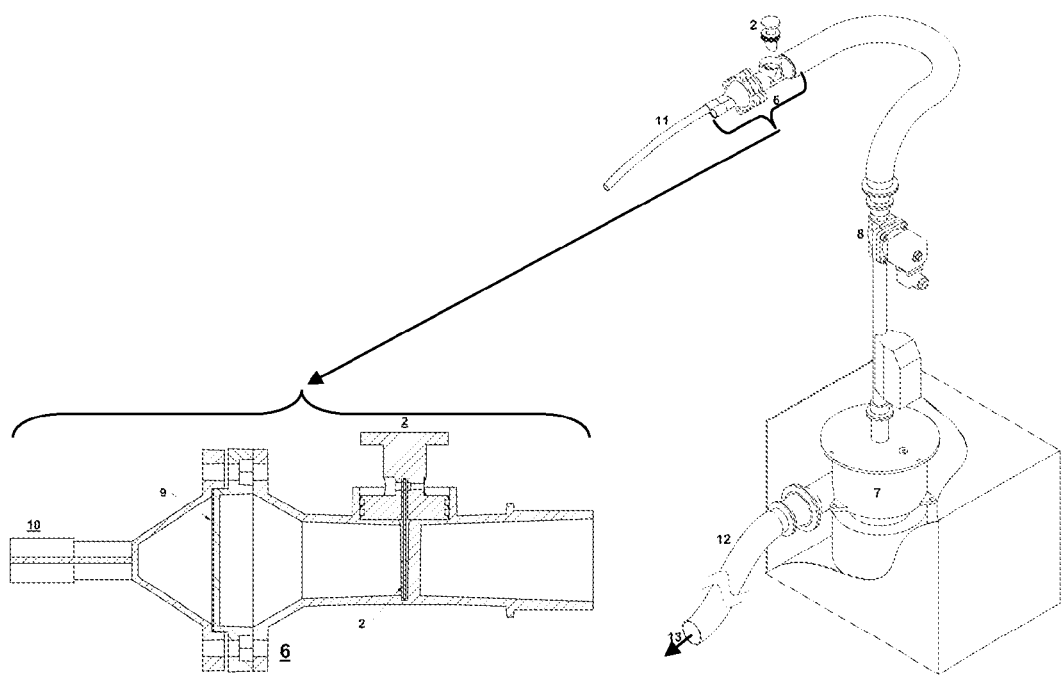
FIG. 2 shows, on the right, a schematic of an embodiment of the sampling system apparatus used in this invention, where a relatively large volume of the gas to be analyzed is passed through the primary filter, where selected vapor species are captured. The figure on the left presents the disposable part of the sampling system. Note the particle pre-filtering stage located upstream the primary filter, included in a preferred embodiment.

FIG. 2 shows a preferred embodiment of a disposable sampler designed to collect the sample vapor. The sampler includes an inlet (10) that can be connected to various implements in order to sample air from various spaces. These implements include among others a polytetrafluoroethylene (PTFE) tube (11) that can be inserted into a pallet, a truck, etc., from which gas is to be sampled. Following the inlet (10) is a prefiltering stage (9), which preferably is in the form of a prefilter, introduced to remove particles and avoid their collection in primary filter (2). For illustrative purposes, the prefiltering stage (9) shall be discussed as being a prefilter. Other means to remove or separate from the sample stream particles larger than a certain size are also included in this invention, such as with an impactor. A preferred alternative embodiment is an impactor, but other well known devices such as inertial separators (virtual impactors, cyclones), etc. are also included. Both the prefilter (9) and the primary filter (2) are backed downstream by a plastic mesh (Acrylonitrile butadiene styrene, ABS) to keep them in place against deformations due to the large flows of sample gas passed. Unlike conventional prefilters having typically a particle size cutoff in the range of 100 µm, this prefilter has a size cutoff typically smaller than 25 µm, and preferably of 10 µm, so as to remove most particles containing sample and therefore base the detection process primarily on species in the vapor phase. Prior to sampling, the primary filter (2) is introduced in its holder (6), where it fits tightly so as to avoid ingesting clean background air instead of air coming through the inlet (10) carrying the desired sample. The primary filter (2) is removably secured to the holder (6) to allow for later removal thereof. Various modes of securement may be utilized including a threaded, bayonet or snap-fit engagement. The sampling system elements upstream of the filter are preferably disposable, so as to avoid contamination of the primary filter (2) by material collected during a previous sampling operation on the filter holder (6) or on other parts of the sampler. The flow of sample is drawn through the primary filter (2) for a desired period by pump (7), whose outlet flow is driven through a tube (12) into a region sufficiently distant to avoid contamination of the environment surrounding the analyzer by the rejected sample gas (13). A no-return valve (8) is preferably interposed between the primary filter (2) and the pump (7) in order to avoid retrograde entry of ambient gas through the generally highly contaminated pump (7) into the vicinity of the primary filter (2). Such a situation could otherwise easily present itself when the pump (7) is turned off, either before the beginning or after the end of the sampling period, while the primary filter (2) is either installed or removed. A lesser level of upstream contamination may still occur via vapor diffusion. For this reason it is preferable to turn the pump (7) on immediately after connecting a new disposable filter holder (6) with its new primary filter (2) to the line leading to the pump (7) through valve (8).

Figure 4:
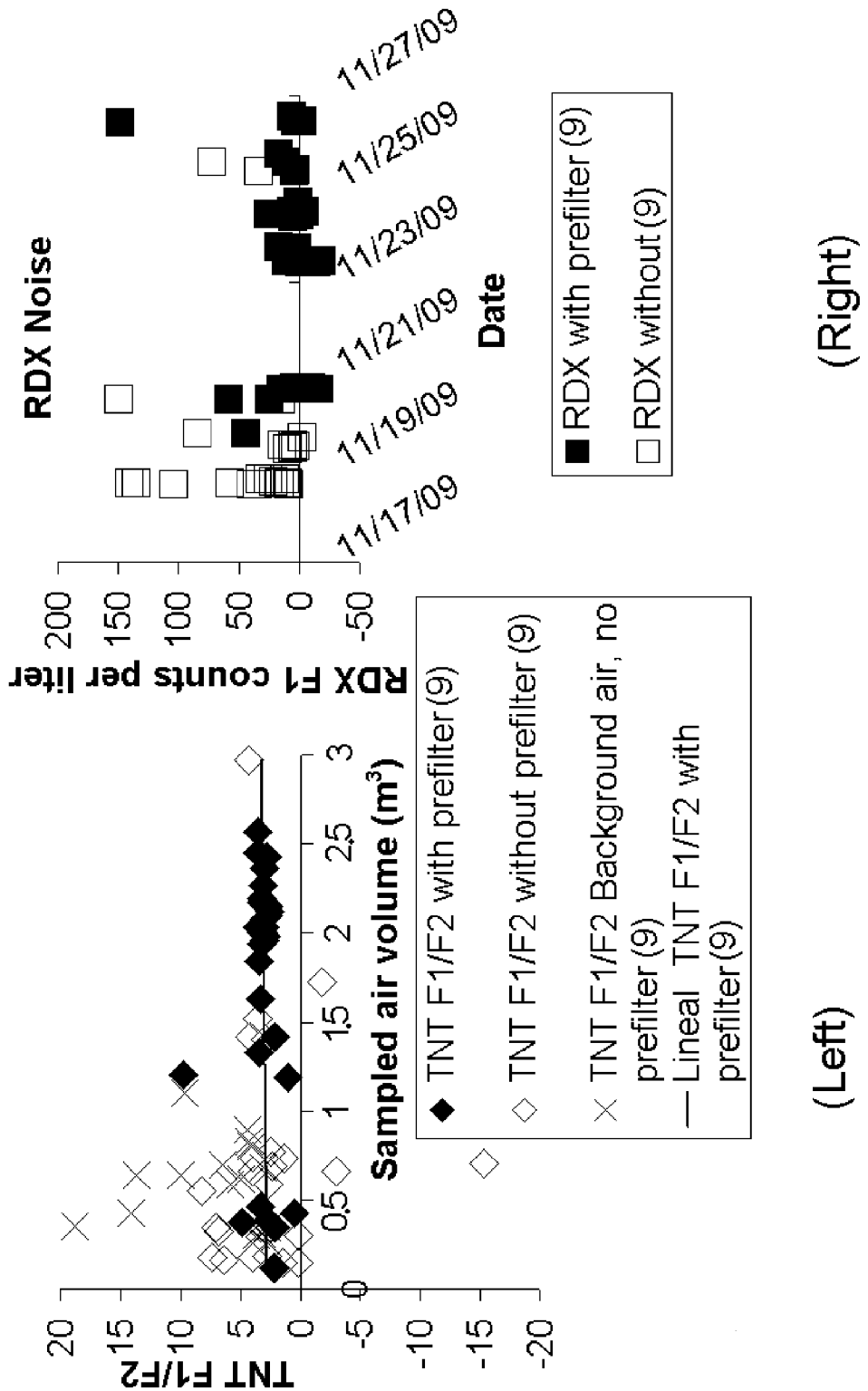
FIG. 4: Illustrates the effect of the prefilter in reducing the noise level.

Several quantitative measures of the improvement produced by the new sampling system are shown in FIG. 4. The left plot shows the ratio of two fragments of the TNT peak measured in the triple quadrupole mass spectrometer upon desorbing a plurality of primary filters having collected ambient air, some with the prefiltering stage and others without it. The ratio should be close to 3 for TNT, and a departure from this value is indicative of chemical noise from a contaminant different from TNT. The horizontal scale is the volume of gas sampled. It is immediately clear that the noise disappears by using a 5 µm prefilter and sampling more than about 1000 liters, and is otherwise fairly large. The right plot shows the background signal of the detector at the mass channel corresponding to RDX, showing similarly a substantial reduction in the noise as a result of using a 5 µm prefilter. The one case shown of high RDX noise (−149 counts/lit) was due to accidental contamination.

Ambient contamination is produced by the effluents of the sampling system and the Analyzer. It is therefore important to drive these contaminated gases outside the enclosed space(s) in which the sample and the Analyzer are located, including possibly driving the contaminated gases outside the relevant building. For the same reason, the disposable filter holder (6) component of the sampler should not be carelessly discarded within any enclosed working space.

This problem was solved by systematically releasing the effluents from the Analyzer and the sampler not within the enclosed working space(s), but outside it. The need for this practice follows from the fact that the ionization efficiency of vapors is relatively small, so most of the vapor sampled is not consumed, but returned to the environment. Even better results were obtained by releasing these effluents at some distance from the enclosed working spaces, for instance, at the end of a chimney outside the relevant building. Use of relatively leak-tight windows and air conditioning tubes is also most desirable to avoid return into the Analyzer of some of these released contaminants.

Figure 5:
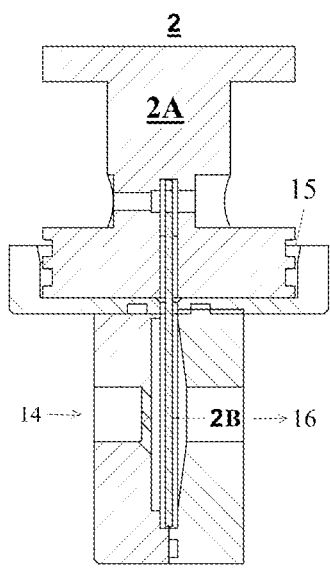
FIG. 5. Shows various components of the desorber.

Once the primary filter (2) is removed from the sampling system, it is preferably introduced into a clean container (preferably an air tight container) to avoid contamination during the period between sampling and desorption. The primary filter (2) includes a handle portion (2A) for handling, with a filter (2B) (vapor collector) fixed thereto. The desorber is shown in more detail in FIG. 5. Several special characteristics distinguish it from other desorbers in other sampling systems. One taught in U.S. Ser. No. 12/686,669 is the use of unusually small sample flow rates (0.1-0.5 lit/min), substantially less than the sampling flow into a typical modern API-MS. This feature avoids diluting with carrier gas the limited sample captured by the primary filter, as well as increases the ionization probability as explained in Ser. No. 12/686,669. U.S. Ser. No. 12/686,669 is incorporated by reference herein. Another important feature is that the clean carrier gas (14) entering the desorber is preheated to the desired desorber temperature. This feature may seem trivial, but it is in fact not. Our early desorbers were commercial, and did not have this feature. It took some effort to realize that the desorption process did not take place uniformly over the diameter of the filter, leading to a non-ideal desorption history and poor use of the sample. The desorber has a leak tight housing (15) where the primary filter (2) is introduced. The same feature is present in the sampling system. The primary filter (2) may be secured using any of the various modes of securement discussed above with respect to the filter holder (6). The heating process is controlled by the same software launching the measurement process of the DMA and the MS. Once most of the sample has evaporated from the filter (as determined by the detector response), the desorber temperature is increased substantially for another set period in order to achieve a thorough decontamination prior to the analysis of another primary filter. Primary filters are typically loaded in the sampling system for periods from one or a few minutes up to 10 minutes, while the desorption process and the final cleanup take about one minute. Sixty samples/hour may therefore be typically analyzed with this detector.

The desorber (1) is followed by a variant of the ionizer (3), some of whose details have been described by Vidal in Ser. No. 12/686,669. The gas (16) leaving the desorber and entering the ionizer is contained within a conduit whose temperature is carefully controlled to avoid condensation of the vapors released from the filter at the desorber.

High boiling point electrospray: when SESI ionization is employed it is important to use electrospray solvents with boiling points higher than the gas temperature to permit proper spraying while the hot gas is in direct contact with the cloud of drops produced by the electrospraying tip (17). Pure solvents generally produce large drops, while better ionization is provided by smaller drops. To favor their production it is important to add the proper ionic additive to the solvent. When promoting negative ionization of explosives, a concentration typically larger than 0.01% by volume of chloride or other halogen ions in acid or salt form is desirable. Other ionizers such as those based on a corona discharge, a radioactive source or other sources of ionizing radiation are also included in this invention. We have implemented a high temperature SESI electrospray as part of this invention based on high boiling point solvents. Many high boiling point solvents are available. For instance, Riddick et al. (1986) order their vast compilation of solvent properties according to boiling point, from which numerous solvents with boiling temperatures $T_b$>150° C. can be identified. However, more than a high boiling point is required for a successful SESI device. The solvent needs also to be available in high purity (to avoid creating too many undesirable or uncontrolled impurity ions). It must be relatively polar in order to become sufficiently conducting to produce very small drops (Fernandez de la Mora and Loscertales, 1994). It must further have a moderately low surface tension in order for a Taylor cone to be stable against electrical discharges, particularly for negative ionization (Fernandez de la Mora, 2007). All these properties except the high boiling point are met by combinations of water with relatively polar organic solvents. Of these, the most widely used is 50/50 water/methanol, first introduced in Fenn's pioneering work on electrospray ionization (Fenn et al., 1989). A few polar solvents of relatively high boiling points are listed in Table 1, with a note on those that are presently commercially available in high purity for high performance liquid chromatography (HPLC) or liquid chromatography mass spectrometry (LC-MS) grade. Comparably polar and high boiling liquids are familiar to those skilled in the art and can be generally selected from the group consisting of amides, alcohols, glycols, esters, ketones, organic carbonates, organic phosphates, and their mixtures.

TABLE 1

Properties of several solvents: $T_b$ = boiling temperature; $\gamma$ = surface tension; $\epsilon$ = dielectric constant. $\mu$ = viscosity coefficient.

| Solvent | $T_b$ (C.) | $\gamma$ (dyn/cm) | $\epsilon$ | $\mu$ (g/s/cm) | HPLC |
|---|---|---|---|---|---|
| Dimethylformamide (DMF) | 153 | | | | Yes |
| N-Methyl 2-Pyrrolidone (NMP) | 202 | 40.7 | 32.2 | 0.0166 | Yes |
| Dimethyl sulfoxide (DMSO) | 189 | 43 | 46.4 | 0.02 | Yes |
| 1-Octanol | 195 | 27 | 10.34 | 0.074 | Yes |
| 2-heptanol | 159 | | 9.21 | 0.065 | |
| Formamide (FM) | 210.5 (dec) | 53.8 | 111 | 0.0376 | No |
| Propylene carbonate (PC) | 241.7 | 41.93 | 64.9 | 0.028(20 C) | No |
| Tributyl phosphate (TBP) | 289 | 28 | 8.91 | 0.034(25 C) | No |
| Sulfolane | 287 | | 43.2 | 0.103(30 C) | No |

Commercial availability of HPLC grade solvent is a convenient feature, even though its lack can be compensated by in-house purification. The most polar solvents listed in Table 1 and available in HPLC grade are DMF, NMP and DMSO. NMP can be electrosprayed by adding to it some special salts or acids (Ku et al. 2004; Ude et al. 2006), but its properties are borderline, which limits its effectiveness as an ionizer. DMSO is an excellent choice for ionization in positive mode. In negative mode its relatively high surface tension makes it difficult to spray, though this problem can be alleviated by mixing it with a low surface tension solvent. An excellent additive for surface tension reduction is 1-octanol, or another high boiling alcohol. 1-Octanol should not be added in excessive proportions, as its modest dielectric constant would then lead to poor electrospraying. For instance, a mixture of DMSO/1-Octanol 75/25 vol. produces excellent negative mode electrosprays. Note that it is much easier to stabilize such negative sprays at elevated temperature (T~150° C.) than at room temperature due to the reduction of the surface tension at increasing temperature. Those skilled in the art of electrospraying can similarly find alternative mixtures achieving high boiling point, good electrosprayability and moderate surface tension by combinations of polar solvents such as DMF, formamide, propylene carbonate, sulfolane, etc., mixed with less polar solvents of lower surface tension. For instance, if a boiling point higher than 200° C. is desired, a mixture of sulfolane and tributylphosphate is an excellent option. Note however that the two solvents must be purified. Also, sulfolane freezes above room temperature, so, depending on the proportion of TBP added, the whole electrospray solvent line may need to be heated.

The notion of using high boiling point solvents for SESI of heated vapors may appear at first sight as evident to those familiar with the fields of vapor analysis and SESI. The literature on SESI and related methods is in fact substantial (see the recent review by Fernandez de la Mora, 2011). Much of this literature is concerned with gas chromatography, where heating the gas sample to temperatures in the range of 150° and above is common. Yet, none of these studies has relied on electrospraying high boiling point liquids. As already discussed, the most advanced SESI configuration used at elevated gas temperature has involved the use of water-cooled electrosprays of conventional (low boiling point) solvents. The conventional-wisdom barrier against the use of high boiling point solvents provides a first reason not to follow this path. Low volatility solvents are evidently a source of hazard in conjunction with expensive equipment such as mass spectrometers, whose vacuum system is generally unheated. If unevaporated solvent drops are ingested in the system, they will survive in its interior for long periods. We have in the past used room temperature electrosprays of the solvent formamide for basic research involving borrowed mass spectrometers, never without serious objections on the part of the instrument owner. If such brief uses raised eyebrows, the notion of a long term use of comparably volatile solvents would be immediately rejected by most. Particularly when a seemingly far simpler and much less potentially damaging solution is available in the form of a water cooled electrospray source. Furthermore, water/methanol has been the workhorse of electrospraying for so long, that the very notion of using an unusual and apparently dangerous solvent for the same purpose is highly unappealing. Finally, there has been no awareness of any advantage of high boiling point solvents over the cooled water/methanol electrospray. Our proposal therefore does not appear to the trained eye as an obvious cure for any clearly perceived problem in existing SESI sources. The problem we aim at curing is real, but it has been previously unperceived. Our aim is to increase the efficiency of the ionization process. This calls for physical contact between the vapors and the high density region of the spray of charged drop, which is within microns from the tip of the electrospraying meniscus. The spray of high boiling point liquids permits this close contact, while the cooled spray of water methanol does not.

SESI Electrospray contamination is another problem solved in the present invention, which affects specially the detection of Ammonium Nitrate. Under equilibrium conditions, when condensed ammonium nitrate coexists as an aerosol with ammonia and nitric acid vapors, the product of the concentrations of ammonia and nitric acid vapors is a constant. Even under conditions below this saturation equilibrium, in the absence of ammonium nitrate aerosol, both ammonia and nitric acid are often abundantly present in the atmosphere from natural and industrial sources. How could one then infer the presence of ammonium nitrate from its volatile components if its two volatile makers are so pervasive in the atmosphere? One answer to this question included in this invention is that indeed, independent and abundant sources of ammonia and nitric acid exist in the atmosphere, but the ratio $NH_3/NO_3H$ differs from one source to the other. This ratio can vary from almost zero to almost infinity depending on source conditions, but should be close to unity in the vicinity of a substantial sample of condensed ammonium nitrate. It may sound paradoxical, but one could in principle detect a package of ammonium nitrate even in an atmosphere having reached saturation conditions leading to the formation of ammonium nitrate aerosol. The reason is that this aerosol is typically formed in the atmosphere from separate gas phase sources of $NH_3$ and $NO_3H$ (rather than from condensed ammonium nitrate) when the product of their concentrations reaches a critical value, yet the $NH_3/NO_3H$ ratio may take any value. In contrast, when ammonia and nitric acid are released from condensed $NO_3NH_4$ by the opposite reaction, the $NH_3/NO_3H$ ratio will immediately shift from its initial ambient value to a value closer to unity. Therefore, by monitoring both vapors periodically one can follow closely their background concentration. Any occasional drastic departure from this background can be taken as a probable sign of the presence of either ammonium or nitrate salts (including nitrate explosives), or concentrated ammonia or nitric acid. Other readily measurable signals would ordinarily serve to strengthen or weaken the suspicion of the presence of nitrate-based explosives. For instance, ammonium nitrate is oxygen rich, so its effectiveness as an explosive is generally increased by mixing it with hydrocarbon fuels. These in turn are generally far more volatile than even the most volatile explosives, and are therefore easily detected by many forms of olfaction. The bouquet of nitrate-based explosives is consequently identifiable by a number of simple strategies resting on the general considerations just discussed. Many variations of this method of detection can be devised by a skilled chemist. For instance, the inconvenience of a double analysis in positive and negative mode is not strictly essential. If one probes periodically the background concentration of only nitric acid, its sudden shift would be almost as sure a sign of the presence of condensed nitrate as would the shift in the $NH_3/NO_3H$ had both vapors been probed.

Reagents can also be introduced in the gas phase for corona ionization, but only as neutral vapors that then need to be converted into ions. This discussion highlights one potential disadvantage of SESI with respect to corona ionization, where no solvent is required. Corona ionization in air or nitrogen, however, produces abundant nitrate ions via gas phase reactions. On the other hand, it is possible in SESI to greatly reduce ionizer contamination by choosing very pure electrospray solvents and reagents.

In our preferred embodiment the Analyzer includes first a DMA, though sampling the ions directly into the mass spectrometer is sometimes also of interest. The DMA is a very useful element in increasing the resolving power of the Analyzer, and hence distinguishing the desired vapors from others having very close masses and fragmentation patterns not unambiguously distinguishable by mass spectrometry alone. However, successful coupling of a DMA to an ionizer to achieve sub-ppt sensitivities requires numerous unprecedented precautions now discussed.

Figure 6:
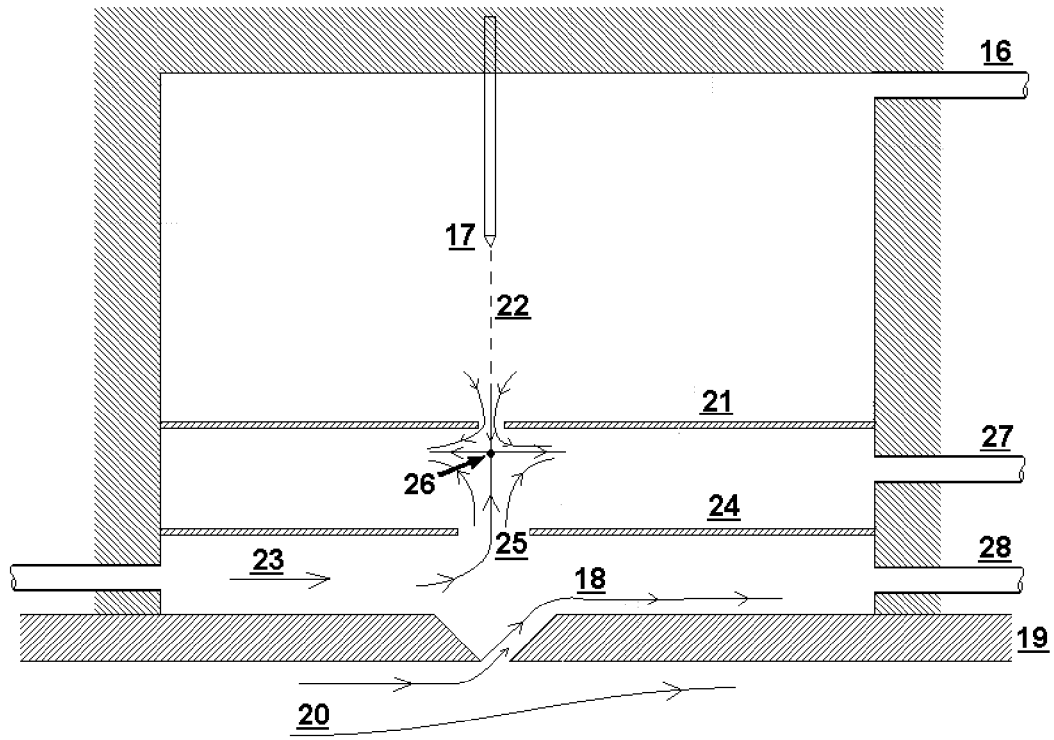
FIG. 6 shows details of the coupling between the ionization region and the analyzer.

The coupling described by Vidal in Ser. No. 12/686,669 between the ionizer and the analyzer is shown schematically in the upper part of FIG. 6 for the special case when the analyzer is a DMA. Vidal's coupling relies on drawing the ionized vapor from the ionization region into the entry slit of the DMA (or orifice to the MS) by means of electric fields. When using a DMA it is important to preclude the ingestion of un-evaporated drops or low mobility clusters from the ionizer into the DMA. This is particularly important when using low volatility liquids, especially when the temperature of the DMA is lower than that in the desorber and the ionizer. Otherwise such drops would penetrate in the DMA providing a source of vapors that could condense on the analyte ions. This is often undesirable, as the electrical mobility of these ions would be affected by vapor attachment. Given sufficient vapor in the DMA, various solvation states of each ion may be simultaneously present, while only one can be efficiently passed by the DMA into the MS. These eventualities may be avoided by use of a counterflow of gas from the interior of the DMA into the ionization region. Note that the electric velocities of the ions are unusually high in Vidal's Ser. No. 12/686,669 ionizer, whereby a proportional increase of the velocity of the counterflow gas is necessary to preclude access of low mobility ions and drops into the DMA interior. One approach to exclude such contaminants from entering into the DMA has been described in U.S. Pat. No. 7,928,373 by Rus et al., which is incorporated by reference herein. They operate the DMA in closed flow circuit, and continuously inject a certain flow Q of clean gas into that circuit. Part of this flow exits the DMA as sample to the MS. The remaining portion exits the inlet slit of the DMA towards the ionization region in the form of a jet of counterflow gas (18). This exiting jet then opposes the entry of neutral gases and low mobility ions towards the interior of the DMA. Not taught in U.S. Pat. No. 7,928,373 but relevant to the present invention is the fact that this counterflow jet (18) does not exit normally to the direction of the DMA flow, but proceeds instead in a direction as close as possible to the direction of the main DMA flow. It is therefore attached to the downstream exterior lip to the inlet slit formed on the upper DMA electrode (19), and moves initially close to parallel to the DMA flow. The effectiveness of this counterflow jet is therefore limited by its direction as well as by its rather large velocity, comparable to the velocity in the main DMA flow (20). An additional complication in the coupling of Vidal's Ser. No. 12/686,669 ionizer to this DMA results from the fact that the counterflow gas heading towards the impact plate (21) of the ionizer is presumed to move along the axis of the orifice or the symmetry plane (22) of the slit leading to the analyzer, while we have just seen that this is not the case for the DMA counterflow. The present invention therefore has introduced the alternative counterflow configuration shown schematically at the bottom of FIG. 6. Instead of coinciding with the jet (18) coming from the DMA, the counterflow gas (23) is here provided separately, and is passed through a new intermediate plate (24). As a result, this gas (23) exits the hole (25) drilled in plate (24) to form a new jet with the symmetry appropriate to meet frontally the sample flow jet. This frontal collision forms the stagnation point (25), similarly as in Vidal's ionizer. The gas brought by these two jets into the impact region is similarly removed through exit line (27), and an electric field is maintained between plates (21) and (24), exactly as in Vidal. A comparable field must also be maintained between plate (24) and the upper DMA electrode (19), such that ions are quickly driven from the ionization region through the openings in plates (21) and (24) into the analyzing region of the DMA. Once the new chamber described is added to Vidal's Ser. No. 12/686,669 ionizer, there is no need for the jet (18) exiting the DMA. This flow can be allowed if desired, but then it must exit through line (28) to avoid interfering with he counterflow gas (23), which one wishes to be as unperturbed as possible.

This invention includes an alternative embodiment of the coupling of the DMA to the ionizer useful in cases when the approaches discussed to avoid ingestion of vapors in the DMA circuit are considered too complex. In one preferred mode of operation of the ionizer, a mixture of DMSO/Octanol (75/25 volume percent) seeded with a source of halide ions is used for electrospray ionization. The temperature in the ionizer is about 200° C., close to the boiling point of the solvent, so that a substantial quantity of solvent vapor is present in the ionizer. If even a modest fraction of this vapor is able to penetrate into the DMA circuit, the detector sensitivity will decay considerably over time. This is in part due to spreading of the ions among various solvation states, and also because the mean electrical mobility of the various analyte ions drifts as the quantity of solvent in the circuit increases, and with it the level of ion solvation. An effective approach to eliminate ion solvation by solvent vapors is to increase the temperature of the circulating gas in the DMA circuit. Note however that this circulating flow must be maintained by a pump moving of the order of one thousand liters per minute. This may be achieved at moderate pump weight and power by special pumps similar to those used in vacuum cleaners. These pumps, however, are generally not designed to run at temperatures of 150-200° C. because the life of the pump is reduced. Also, lubricant vapors may be injected from the pump into the circulating gas, making the situation worse rather than better. A temperature in the range from 70 to 100° C., preferably 80° C. offers a good compromise, as it is high enough to greatly reduce solvation problems, and low enough to preclude pump problems.

As already indicated, heating of the surfaces in contact with the sample gas is meant to avoid memory effects from adsorption of sample vapors on cold surfaces. Because the plate is at high voltage, Joule heating with an alternating current is a convenient solution. However, the desired close proximity of plate (21) to the upper DMA electrode (19) may then induce an oscillation in the DMA voltage, drastically decreasing DMA resolution. One solution is provided by the use of plate (24), which is bathed by clean gas (23) on the analyzer side, and does not strictly require heating. This plate may then be held at a fixed potential and designed so as to shield the DMA electrode to greatly reduce the ripple induced on (19) by voltage variations in (21). Another solution is provided by the use of heating elements in (21) relying on small resistances, with higher currents and considerably smaller voltage drops. In another scheme, direct current would be used for heating the plates. Those familiar with the fields of heating and induction could provide solutions to this difficulty once being made aware of it. However, because the identification of the existence of this problem has been difficult, its solution is included within this invention.

Returning now to the DMA circuit, typical operating conditions in recirculating flow produce by themselves significant heating in the pump. If unchecked, this heating not only eventually damages the pump. In addition it could release vapors from pump components which may be incorporated into the DMA circuit and attach to the ions analyzed modifying their mobility. This problem may be partly alleviated by operating the DMA circuit at a pressure slightly higher than atmospheric pressure, so that vapors produced in the pump outside of the compression circuit leak through the axis of the rotor from the closed DMA circuit into the atmosphere rather than vice-versa. In one embodiment, the DMA circuit is maintained at a slight superatmospheric pressure by communicating it with the atmosphere through a flowmeter and verifying that gas flows from the closed circuit to the atmosphere. Another important measure to reduce or eliminate pump damage and contamination of the circuit is to cool either the pump motor or the circulating gas. Such pumps are conventionally cooled by a fan blowing surrounding atmospheric air, and this effect can be augmented by use of more powerful external fans or other cooling methods employed by those familiar with the art. In addition, our preferred embodiment includes an air cooler in the closed circuit, similarly as in racing car, truck or tractor radiators. The gas in the closed circuit circulates through the fins of the radiator (designed to allow the high circulation flows of the DMA without substantial pressure drop). These fins are in turn actively cooled from outside with a fan blowing room air. The circuit temperature needs to be stabilized in order to fix the electrical mobility of the ions analyzed. A variation of this temperature could lead to incorrect assignment of the DMA voltage and reduced transmission of the desired ions to the MS. The present invention includes an active temperature control of the gas temperature in the DMA circuit. The control system keeps the temperature at a preset constant value via active control by sensing the temperature in the DMA gas flow following the analyzing region, and providing heating or cooling instructions to either the cooler just described or to a heating bundle surrounding a part of the recirculation circuit. In one preferred embodiment, the gas flowing through the DMA is kept in the vicinity of 80° C. This suffices to mitigate undesirable clustering effects of vapors having for some reason penetrated into the circuit, but is still low enough for proper operation of the pump. It is equally important to actively stabilize the pump to maintain the gas velocity constant within 1% or better. This is typically not possible by simply connecting the pump to a wall socket, as the provided voltage is not sufficiently steady and depends on the power drawn by other elements such as air conditioning. Our preferred embodiment measures the speed of pump rotation and adjusts accordingly the power supplied to its motor so as to keep this angular speed constant.

Figure 7:
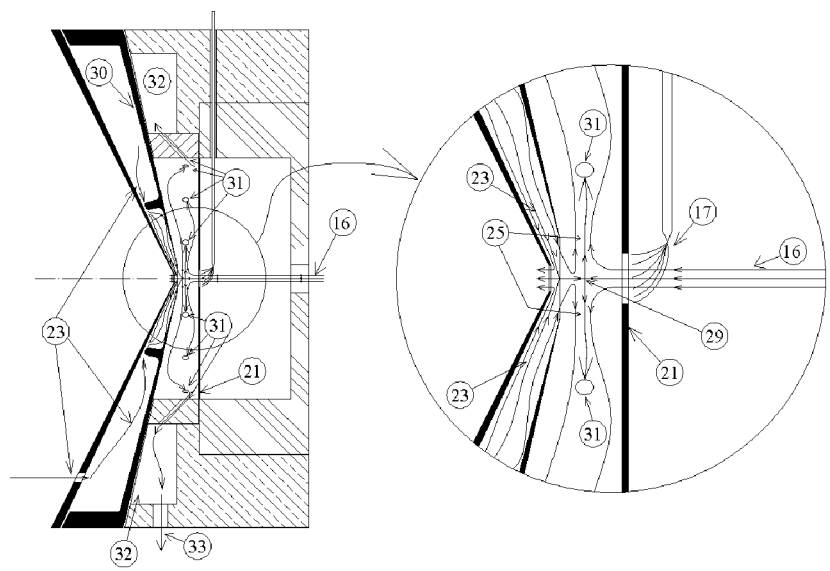
FIG. 7 Shows details on how to maintain the symmetry of the impinging flows below plate (21) when the analyzer inlet is cylindrically symmetrical.

Returning now to the ionizer and its coupling to the analyzer, it is important to introduce further refinements in the symmetry of the various flows involved, particularly when a stagnation point (26) is formed upon frontal impact of the sample flow and the clean gas flow (23) downstream from the opening in the first plate (21). The greater the symmetry achieved in the impact region, the smaller the likelihood of penetration of clean gas into the ionization region. A preferred approach to achieve this goal is first illustrated in FIG. 7 for the simpler case (enjoying approximate cylindrical symmetry) resulting when the ionizer is coupled to a mass spectrometer. The coupling illustrated corresponds to the particular case when the inlet to the MS is an axi-symmetrical orifice. In this case the coupling is greatly simplified not only by the prevailing circular symmetry, but also because the counterflow gas leaving the analyzer through opening (29) in the conical curtain gas plate (30) can be heated, and also because its flow rate is substantially higher than that of the (also heated) sample gas flow (16). Unlike in the DMA, which tends to operate colder than the ionizer, whereby the clean gas (23) is relatively cold when reaching the impact region (26), here, plate (21) is maintained passively hot by these surrounding gases and suitable insulation on its supports. Symmetry in the jet of sample gas exiting the opening in (21) is naturally assured by its small flow rate and associated rather small flow velocity in the ionization region. Given the larger magnitude of the corresponding flow rate of counterflow gas (23) entering the impact zone through opening (29) its symmetry is not automatically satisfied, but must be forced by the geometry of the region through which it flows upstream from (29). Similarly the flow of the gas downstream from the stagnation point (25) must be drawn with cylindrical symmetry. This is achieved in the design of FIG. 6 by pulling it out of the impact region through numerous symmetrically placed perforations (31). These many holes connect the impact region to an exhaust chamber (32), from which the flow is drawn (asymmetrically) out of the instrument via a single conduit (33). In both cases the symmetry of the flow in an incompletely symmetric geometry is guaranteed by the right balance of pressure drops in the various key components. For instance, the pressure drop for the flow to move from one end to the other within the exhaust chamber (32) is very small compared to the pressure drop required for the gas to flow through each of the perforations (31). Consequently, since these various holes are geometrically identical, each passes essentially the same flow into the exhaust chamber. And because the spacing between the various holes is uniform, the gas is pulled out of the ionization chamber almost axisymmetrically.

Similar considerations apply when coupling the ionizer to a DMA. In this case, we have already noted that the clean gas (23) may be relatively cold, so plate (21) needs to be actively heated. Also, the openings in the various plates and in the inlet to the DMA are no longer circular holes, but linear slits. The right symmetry in the various flows can nonetheless be achieved similarly as before. For instance, the sample gas will naturally form a rectangular jet because here again the gas velocity is small in the ionization region. However, the exhaust gas (27) will not naturally flow symmetrically. The proper flow restrictions with rectangular symmetry must therefore be installed. FIG. 8 illustrates one embodiment of this principle.

Even though our description of the ionizer has referred specifically to plates, elements (21) and (24) need not be flat plates. They may be cones in axisymmetric situations, such as electrode (30) in FIG. 7. When the analyzer coupled to the ionizer has planar symmetry (as in the case of a DMA with a rectilinear inlet slit), these plates may be substituted by "bent plates" (the two-dimensional analogs of cones). One clear advantage of this alternative geometry (illustrated by elements (21) and (30) in FIG. 7) is that these cones or "bent plates" may be placed closer to each other, with considerable advantage in reducing space charge dilution and increasing ion transmission. The term plate in this specification should therefore be interpreted in this broader sense. We shall also refer generally to such non-planar plates as perforated electrodes. Indeed, their purpose is to partially isolate certain regions from each other, providing limited communication between adjacent regions, and permitting establishing electric fields meant to rapidly guide the ions from one chamber to the next.

Coupling of the DMA to the MS has been also described in U.S. patent application Ser. No. 11/786/688, incorporated by reference herein. A particularly efficient way of coupling the DMA to a quadrupole MS that does not increase the time for DMA-MS analysis with respect to that required for pure MS analysis has been described in U.S. Pat. No. 7,855,360, incorporated by reference herein. These various approaches are incorporated in the present invention.

An important aspect of the Analyzer is the procedure to minimize contamination of all key components of the system. A preferred embodiment of the environment of the Analyzer facilitating this goal is shown in FIG. 9. The Analyzer (34) is enclosed in a room or a cabin (35) (subsequently referred to as the cabin), preferably with an air conditioning system (36) to maintain the DMA and the mass spectrometer at a temperature close to that of their specifications to keep accurate mass and mobility calibrations. The fitting of the air conditioning system (36) to the cabin (35) should preferably have no imperfections enabling entry of unfiltered air. The doors (37) and windows to the cabin are preferably leak tight for two reasons. First to avoid entry of vapors and particles from the often contaminated surrounding (for instance in a cargo environment). Second and even more importantly, to preclude entry into the cabin of air contaminated by the explosives analyzed by the detector. For the same reason, the effluent gases from the Analyzer is preferably vented via exhaust tube (38) not only outside the cabin, but also at a considerable distance from it so as to minimize the probability of their return into the cabin through the air conditioning system. When safe disposal of effluent gases at a distance of tens of meters from the cabin is not possible, an equally safe alternative is using two air conditioning entries on opposite sides of the cabin. This should be complemented with an automatic system switching on the upwind and off the downwind entry depending on meteorological conditions. Optionally, portions of the system may be made disposable such as to be replaceable to avoid contamination of future uses. For example, a portion of the system after the prefilter may be made disposable and replaceable. Likewise, the desorber and/or the primary filter as a unit may be replaceable.

A second aspect of the present invention includes an evaluation system for other sensitive vapor detectors trained to recognize certain target odors, but lacking the chemical specificity of a mass spectrometer. One such system would rely, for instance, on canine olfaction. Another would mimic animal olfaction with a multitude of different solid state gas detectors, each responding to a limited family of vapors, with the full set being capable of recognizing many vapors after suitable training. Such detectors may perhaps recognize a familiar scent presented to them, but cannot ascertain the nature or purity of the substance releasing it. It is therefore evident that the vapor standard must be very pure to train a detector of this kind. This is particularly necessary in the case of low volatility target substances, as any trace of a more volatile impurity would tend to produce a far more potent olfactive signature. If the detector is trained with this contaminated target, it will almost surely be incapable of recognizing the uncontaminated substance. Even if it is initially correctly trained, any subsequent contamination of the training sample will rapidly corrupt what was initially properly learned. The evident difficulty of controlling the reliability of such detectors is compounded by many other factors. The training of biological detectors needs to be continuous, pure standards are expensive, and contamination is in the long term unavoidable in repeatedly manipulated samples. This being so with each target substance taken separately, imagine the problem of avoiding cross contamination among the dozen different target substances each trainer needs to manipulate and each dog needs to recognize separately. The TSA's reservations towards such biological detectors are hence readily understood as a simple consequence of the lack of a safe method to train non-chemically specific vapor detectors. The remedy for this problem, however, becomes simple in light of our invention. It involves periodically testing the purity of the standards used to train such detectors, by analyzing them with a chemically specific detector sensitive to ppt concentrations, such as the one described in this invention. More specifically one would (a) provide an uncontaminated environment where to carry out the required testing and training; (b) Provide a highly purified standard for each vapor for which training is required; (c) Generate ppt or sub-ppt concentrations of each individual vapor (i.e., as described by Martinez Lozano et al. in J. Am. Soc. Mass Spectr. 2009, 20, 287-294) to be used for training or testing; (c) provide a protocol to handle each individual standard within said set of standards, so as to minimize cross contamination; (d) provide a protocol to handle said environment so as to avoid its contamination by said standards during training or testing; (e) Occasionally using a chemically specific detector of vapors having sub-ppt sensitivity to test for possible contamination in either said standards, or said doses of individual training vapors.

Much of the discussion has involved the combination of a sampling and a desorbtion system with an analyzer. However, many of the improvements discussed relating to the analyzer, the ionizer and the coupling between both are equally useful for analysis of ambient volatiles directly, without their prior accumulation in a collection device. These separate improvements are also considered part of this invention.

We claim:

1. A method to detect the presence of substances based primarily on the vapors they release to a surrounding gas, involving:
    a) sampling said gas to which said vapors have been released and passing it through a prefiltering stage including means configured for removing particles larger than 25 μm carried by said gas,
    b) passing said prefiltered gas into a vapor capture stage including a collection chamber containing a vapor collector, such that a fraction of said vapors are captured into said vapor collector, said vapors not captured into said vapor collector being residual vapors,
    c) where said vapor capture stage includes at least one contamination prevention means, such that said residual vapors having circulated through said collection chamber during one vapor capture event are not released to the vapor collector during a subsequent vapor capture event into said gas, and therefore are not captured by the vapor collector during said subsequent vapor capture event, and
    d) a desorption-ionization and analysis stage where said vapors captured into said vapor collector are thermally released into a flow of clean gas and passed through an ionization chamber where a fraction of said thermally released vapors are turned into ions, and said ions are finally analyzed and detected in an analytical instrument.

2. The method of claim 1 where said at least one contamination prevention means includes:
    a) said collection chamber is disposed of after use;
    b) said gas is sampled into said collection chamber via a source of negative pressure, said source of negative pressure drawing said residual vapors from said collection chamber, and a no-return valve is introduced between said source of negative pressure and said collection chamber, so as to avoid backflow of said residual vapors into said collection chamber; and
    c) a sample gas outlet flow of said source of negative pressure is released to the atmosphere at a place remote from the location where said sampling of said gas takes place, so as to moderate contamination of the surroundings of said collection chamber.

3. The method of claim 1 where said vapors thermally released onto said flow of clean gas are cleanly disposed of following said ionization and said analysis, such as to avoid contamination of either said analytical instrument or a room or cabin housing it.

4. The method of claim 1 where said analytical instrument includes a mass spectrometer.

5. The method of claim 4 including a differential mobility analyzer.

6. The method of claim 1 wherein the means for removing particles larger than 25 μm carried by said gas includes a prefilter.

7. The method of claim 1 wherein the means for removing particles larger than 25 μm carried by said gas includes an impactor.

8. A method to detect the presence of substances based primarily on the vapors they release to a surrounding gas, involving:
    a) sampling said gas to which said vapors have been released and passing it through a prefiltering stage including means configured for removing particles larger than 25 μm carried by said gas,
    b) passing said prefiltered gas into a vapor capture stage including a collection chamber containing a vapor collector, such that a fraction of said vapors are captured into said vapor collector,
    c) where said vapor capture stage includes at least one contamination prevention means, such that residual vapors having circulated through said collection chamber during one vapor capture event are not released to the vapor collector during a subsequent vapor capture event into said gas, and therefore are not captured by the vapor collector during said subsequent vapor capture event, and
    d) a desorption-ionization and analysis stage where said vapors captured into said vapor collector are thermally released into a flow of clean gas and passed through an ionization chamber where a fraction of said vapors are turned into ions, and said ions are finally analyzed and detected in an analytical instrument, where said vapors are ionized by bringing said vapors into close contact with an electrospray cloud, and where an electrified liquid meniscus producing said cloud is kept at a temperature greater than 100° C., such that said gas can be simultaneously maintained at a temperature greater than 100° C. and kept in direct contact with said meniscus.

9. The method of claim 8 where said liquid meniscus includes liquids with dielectric constants in excess of 10 and ambient pressure boiling points higher than 110° C.

10. The method of claim 9 where said liquids include one of the following:

N-Methyl 2-Pyrrolidone, dimethylformamide, Dimethyl sulfoxide, alcohols containing more than four carbon atoms, Formamide, Propylene carbonate, Tributyl phosphate, Sulfolane, or are more generally selected from the group consisting of amides, alcohols, glycols, esters, ketones, organic carbonates, organic phosphates, and mixtures of one or more of the foregoing.

11. The method of claim 9 where said analytical instrument includes a DMA whose recirculating gas is kept at a temperature higher than 70° C.

* * * * *